United States Patent
Hirano et al.

[11] 3,953,546
[45] Apr. 27, 1976

[54] THIO(DITHIO)PHOSPHORATES

[75] Inventors: Masachika Hirano, Toyonaka; Kunio Mukai, Nishinomiya; Hisami Takeda, Takarazuka, all of Japan

[73] Assignee: Sumitomo Chemical Company, Limited, Osaka, Japan

[22] Filed: July 11, 1974

[21] Appl. No.: 487,670

[30] Foreign Application Priority Data
July 31, 1973 Japan.............................. 48-86569
Apr. 5, 1974 Japan.............................. 49-39319

[52] U.S. Cl................................. 260/938; 424/211
[51] Int. Cl.².......................... A01N 9/36; C07F 9/18
[58] Field of Search..................... 260/938, 944, 964

[56] References Cited
UNITED STATES PATENTS

| | | | |
|---|---|---|---|
| 3,733,375 | 5/1973 | Gutman | 260/938 |
| 3,792,130 | 2/1974 | Stach | 260/944 |
| 3,819,751 | 6/1974 | Dixon | 260/938 |
| 3,839,511 | 10/1974 | Kishino et al. | 260/964 |

*Primary Examiner*—Richard L. Raymond
*Attorney, Agent, or Firm*—Stevens, Davis, Miller & Mosher

[57] ABSTRACT

Thio(dithio)-phosphorate of the formula,

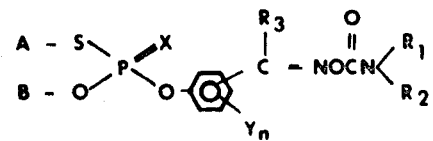

wherein A represents an alkyl having up to 6 carbon atoms; B represents lower alkyl having up to 4 carbon atoms; Y represents halogen, methoxy or ethoxy; X represents oxygen or sulfur; $R_1$ represents alkyl having up to 6 carbon atoms, phenyl, phenyl substituted by halogen or phenyl substituted by lower alkyl having up to 4 carbon atoms; $R_2$ represents hydrogen or alkyl having up to 6 carbon atoms; $R_3$ represents hydrogen or alkyl having up to 6 carbon atoms; and $n$ represents 0, 1 or 2, which is useful as a pesticide.

8 Claims, No Drawings

THIO(DITHIO)PHOSPHORATES

The present invention relates to thio(dithio)phosphorate of the formula (I),

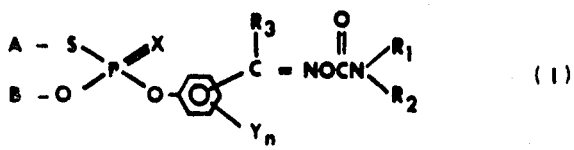

wherein A is a $C_1$–$C_6$ alkyl group, B is a $C_1$–$C_4$ alkyl group, X is an oxygen or sulfur atom, Y is a halogen atom, a methoxy group or an ethoxy, $R_1$ is an $C_1$–$C_6$ alkyl, phenyl, phenyl substituted by halogen or phenyl substituted by lower alkyl having up to 4 carbon atoms, $R_2$ and $R_3$ are each a hydrogen atom or $C_1$–$C_6$ alkyl group, and $n$ is 0, 1 or 2, and to insecticides, nematocides and acaricides characterized by containing the compounds of the formula (I) as an active ingredient, and to the preparation thereof.

The compounds of the formula (I) according to the present invention have not only an extremely strong insecticidal activity against Lepidopterous insects such as tobacco cut worm, cabbage worm, diamond-back moth, tortorixes and stem-borers, but also a strong insecticidal activity against Hemipterous insects such as green rice leafhoppers, planthoppers and aphids, as well as various kinds of insects injurious to agriculture and household horticulture, woods and forests, domestic animals, sanitation and stored cereals; mites; and animal parasitic mites and nematodes.

Many of the homogues having a strong insecticidal activity other than the present compounds give phytotoxicity to crops, while the present compounds have no such the hazard and in addition a low toxicity to mammals. Therefore the compounds of the formula (I) can be used very advantageously as pesticides.

The present invention further relates to
1. a method for preparing thio(dithio)-phosphorate of the formula (I) ($R_2$ is a hydrogen atom) with insecticidal, acaricidal and nematocidal activity characterized in that the compounds are obtained by the addition reaction between oximes of the formula (II),

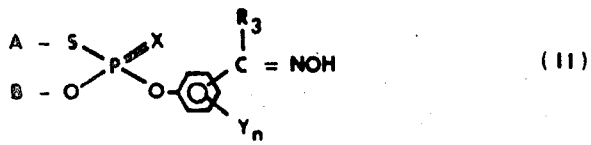

wherein A, B, $R_3$, X, Y and $n$ are same as defined above, and isocyanates of the formula (III), $$R_1NCO \quad\quad (III)$$

wherein $R_1$ is same as defined above, and
2. a method for preparing thio(dithio)-phosphorate of the formula (I) with insecticidal, acaricidal and nematocidal activity characterized in that the compounds are obtained by the condensation reaction, in the presence of acid-binding agent, between oximes of the formula (II) and carbamic acid chloride of the formula (IV),

wherein $R_1$ and $R_2$ are same as defined above.

The above-mentioned process 1 of the present invention can preferably be carried out by the addition reaction between oximes of the formula (II) and isocyanates of the formula (III) in the presence of solvents such as ethers, aromatic or aliphatic hydrocarbons, and preferably, in the presence of the solvents which can dissolve the two starting compounds completely. The reaction temperature and time vary with the solvents and materials used, and, in general, satisfactory results can be obtained at 0° to 100°C for 1 to several 10 hours. In some cases desirable results can be obtained with an addition of catalytic amount of tertiary organic bases.

The process 2 of the present invention can preferably be carried out by the condensation reaction between oximes of the formula (II) and carbamic acid chlorides of the formula (IV) in the presence of solvents such as aromatic solvents (benzene, toluene) and ketones (acetone, methylisobutylketone), and acid-binding agents such as inorganic salts (sodium hydroxide, potassium hydroxide, sodium carbonate anhydrous and potassium carbonate anhydrous) and organic bases (triethylamine and pyridine). The reaction temperature and time vary with the materials and solvents used and, in general, satisfactory results can be obtained at 20° to 120°C for 1 to several hours.

The oximes of the formula (II), a starting material, are novel compounds and can easily be prepared from phosphorate of the formula (V),

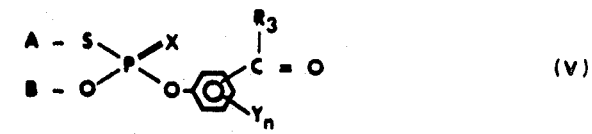

wherein A, B, $R_3$, Y and $n$ are same as defined above, and hydroxylamine. The phosphorate of the formula (V) can be obtained by the condensation reaction between phosphoryl chloride of the formula (VI),

wherein A, B and X are same as defined above, and phenols of the formula (VII)

wherein $R_3$, Y and $n$ are same as defined above, or by the condensation reaction between phosphate of the formula (VIII),

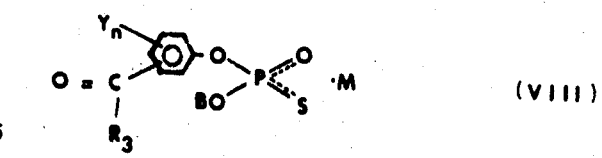

wherein B, $R_3$, Y and $n$ are same as defined above, and M is an alkali metal atom, and halogen compounds of the formula (IX), Hal . A    (IX)

wherein A is same as defined above and Hal is a halogen atom.

As examples of the starting materials used according to the present invention, oximes (II), isocyanates (III) and carbamic acid chlorides (IV), there are exemplified as follows. Oximes:

3-(O-ethyl-S-(n)-propylphosphoryloxy)-acetophenonoxime
4-(O-ethyl-S-(n)-propylphosphoryloxy)-acetophenonoxime
2-(O-ethyl-S-(n)-propylphosphoryloxy)-acetophenonoxime
2-(O-ethyl-S-(n)-butylphosphoryloxy)-acetophenonoxime
3-(O-ethyl-S-(n)-butylphosphoryloxy)-acetophenonoxime
4-(O-ethyl-S-(n)-butylphosphoryloxy)-acetophenonoxime
2-(O-ethyl-S-(sec)-butylphosphoryloxy)-acetophenonoxime
3-(O-ethyl-S-(sec)-butylphosphoryloxy)-acetophenonoxime
4-(O-ethyl-S-(sec)-butylphosphoryloxy)-acetophenonoxime
2-(O-ethyl-S-(n)-propylthionophosphoryloxy)-acetophenonoxime
3-(O-ethyl-S-(n)-propylthionophosphoryloxy)-acetophenonoxime
4-(O-ethyl-S-(n)-propylthionophosphoryloxy)-acetophenonoxime
2-(O-ethyl-S-(n)-propylphosphoryloxy)-propiophenonoxime
4-(O-ethyl-S-(n)-propylphosphoryloxy)-propiophenonoxime
2-chloro-4-(O-ethyl-S-(n)-propylphosphoryloxy)-acetophenonoxime
3-(O-ethyl-S-(n)-propylphosphoryloxy)-benzaldoxime
4-(O-ethyl-S-(n)-propylphosphoryloxy)-benzaldoxime
2-(O-ethyl-S-(n)-propylphosphoryloxy)-benzaldoxime
2-(O-ethyl-S-(n)-butylphosphoryloxy)-benzaldoxime
3-(O-ethyl-S-(n)-butylphosphoryloxy)-benzaldoxime
4-(O-ethyl-S-(n)-butylphosphoryloxy)-benzaldoxime
2-(O-ethyl-S-(sec)-butylphosphoryloxy)-benzaldoxime
3-(O-ethyl-S-(sec)-butylphosphoryloxy)-benzaldoxime
4-(O-ethyl-S-(sec)-butylphosphoryloxy)-benzaldoxime
2-(O-ethyl-S-(n)-propylthionophosphoryloxy)-benzaldoxime
3-(O-ethyl-S-(n)-propylthionophosphoryloxy)-benzaldoxime
4-(O-ethyl-S-(n)-propylthionophosphoryloxy)-benzaldoxime
4-(O-ethyl-S-(n)-propylphosphoryloxy)-2-methoxybenzaldoxime
4-(O-ethyl-S-(n)-propylphosphoryloxy)-2-chlorobenzaldoxime
4-(O-ethyl-S-(n)-propylphosphoryloxy)-2,6-dichloro-benzaldoxime Isocyanates:
methylisocyanate, ethylisocyanate, propylisocyanate, butylisocyanate, phenylisocyanate, chlorophenylisocyanate Carbamic acid chlorides: dimethylcarbamic acid chloride, diethylcarbamic acid chloride, dibutylcarbamic acid chloride The typical compounds of the present invention will be shown as follows which are only given for the purpose of illustration and not to be interpreted as limiting.

(1) 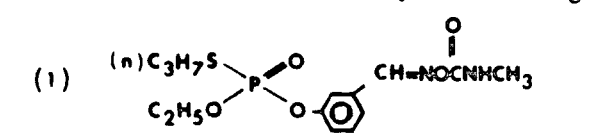

(2) 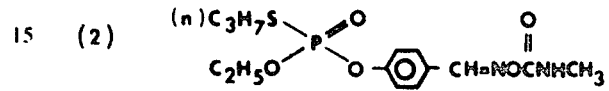

(3) 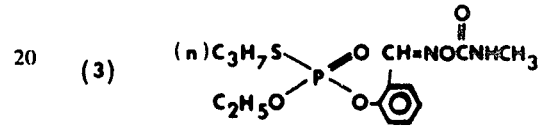

(4) 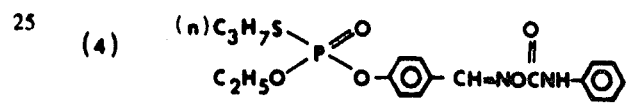

(5) 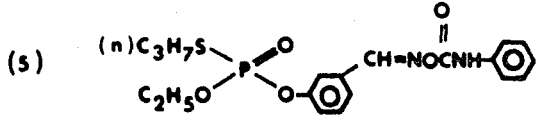

(6) 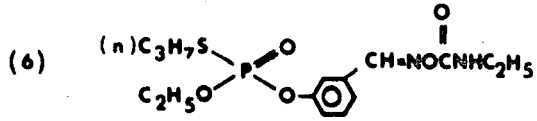

(7) 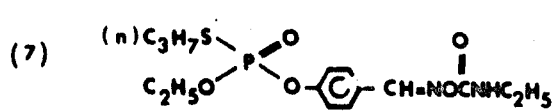

(8) 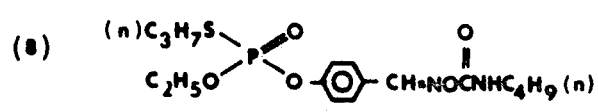

(9) 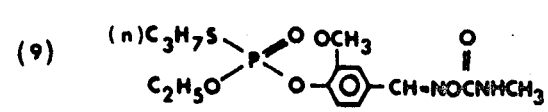

(10) 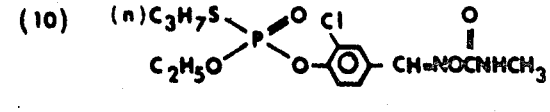

(11) 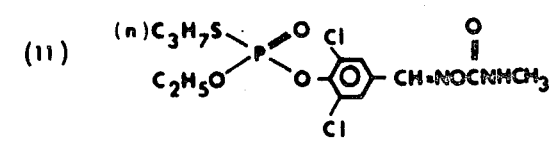

(12) 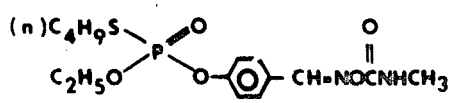
(13) 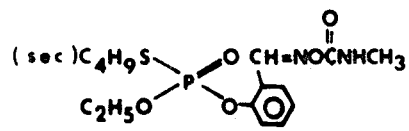
(14) 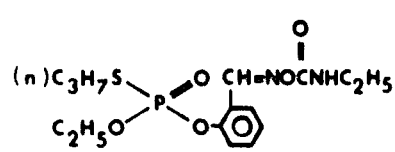
(15) 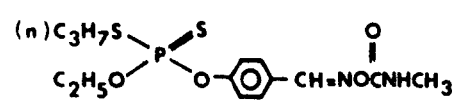
(16) 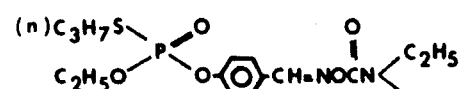
(17) 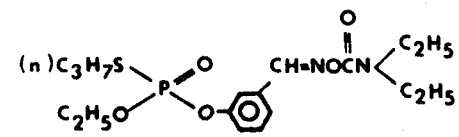
(18) 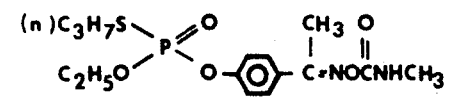
(19) 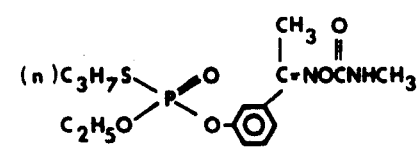
(20) 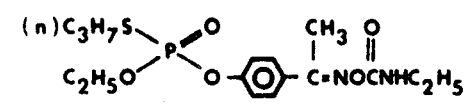
(21) 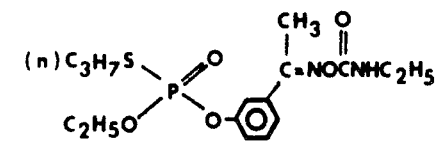
(22) 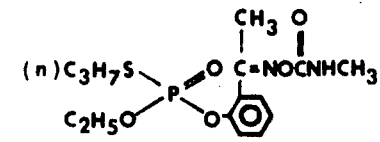
(23) 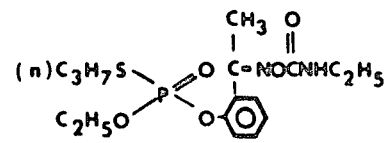
(24) 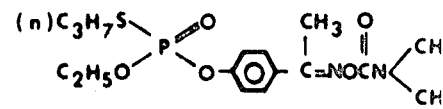
(25) 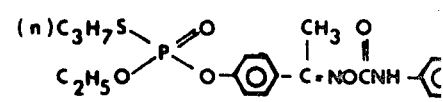
(26) 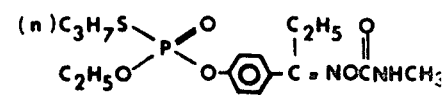
(27) 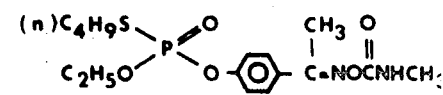
(28) 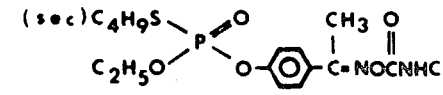
(29) 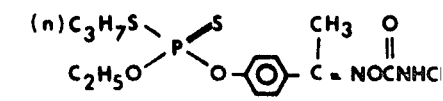
(30) 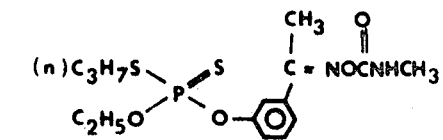
(31) 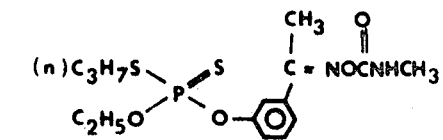
(32) 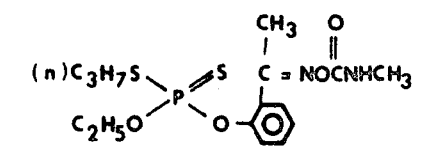
(33) 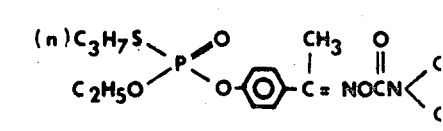

(34) 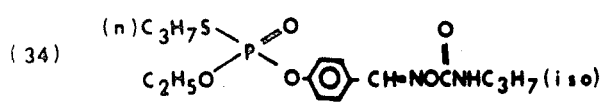

(35) 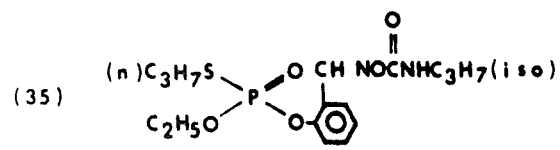

(36) 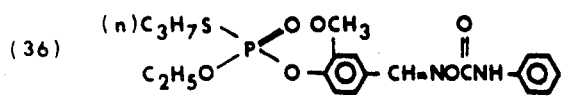

(37) 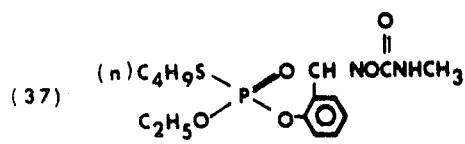

(38) 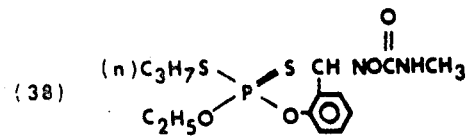

(39) 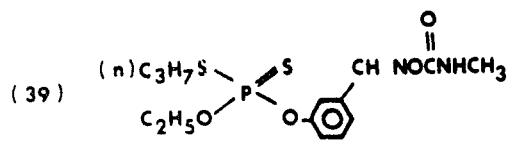

(40) 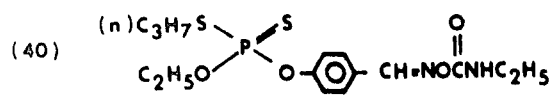

(41) 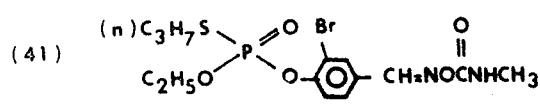

(42) 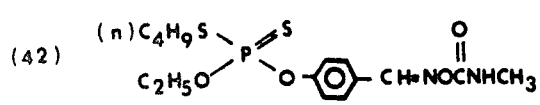

(43) 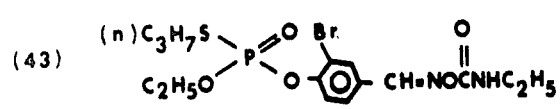

(44) 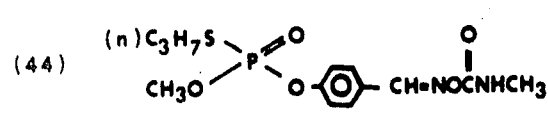

(45) 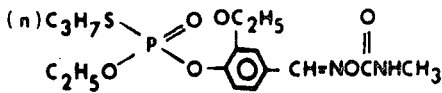

(46) 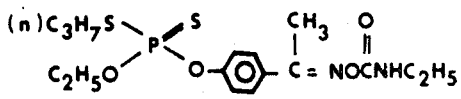

(47) 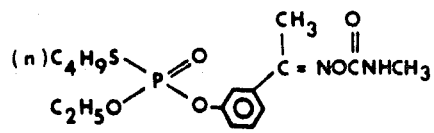

(48) 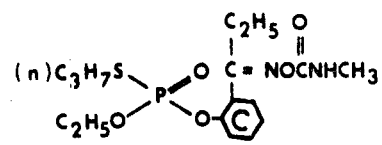

(49) 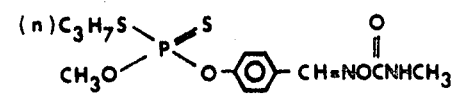

In the practical application of the present compounds, they may be applied alone or in combination with a carrier for the ease of use as a pesticide. The present compounds are formulated, like the common organophosphorus insecticides, into various preparation forms such as emulsifiable concentrates, wettable powders, oil sprays, dusts, coatings, granules, fine granules, aerosols and heating fumigants by the methods well known to the skilled in the art, and are applied in the forms which are suitable for application methods.

Furthermore, the lethal effects of the present compounds can be extended and strengthened in combination with one or more of other pesticides. As examples of the pesticides, there are exemplified organo-phosphorus insecticides such as O,O-dimethyl-O-(3-methyl-4-nitrophenyl)-phosphorothioate, O-ethyl-O-(p-cyanophenyl)-phenylphosphonothioate, 2-methoxy-4H-1,3,2-benzodioxaphosphorin-2-sulfide and dimethoate; organo-chlorine insecticides such as BHC and DDT; carbamate insecticides such as 3,4-dimethylphenyl-N-methylcarbamate and 1-naphthyl-N-methylcarbamate; pyrethroid insecticides such as Allethrin and Tetramethrin; organo-chlorine fungicides such as pentachlorobenzylalcohol and pentachlorobenzaldoxime; and organo-sulfur and organo-arsenic fungicides.

Furthermore, the present compounds can be formulated into multi-purpose compositions in combination with acaricides, herbicides, fertilizers, plant regulators, microbial insecticides such as B.T. and B.M.; synergists; attractants; repellents; insect hormone compounds and other agricultural chemicals, with a synergistic effect in certain combinations.

The present invention will be illustrated with reference to the following preparation examples which are only given for the purpose of illustration and not to be interpreted as limiting.

PREPARATION 1

Emulsifiable concentrates

50 Parts by weight of each of the present compounds, (1)–(6), (9), (10), (13), (17)–(23), (26), (27), (30), (33)–(37), (40), (45), (47) and (48), 30 parts by weight of xylene and 20 parts by weight of Sorpol 2020 (a registered trade mark of Toho Kagaku Co.) were mixed in a proper order. Twenty-eight uniform emulsifiable concentrates were thus obtained. They are each applied in a diluted form with water.

PREPARATION 2

Wettable powders

40 Parts by weight of each of the present compounds, (1)–(3), (5)–(8), (10)–(20), (22)–(25), (27), (28), (30)–(49), and 5 parts by weight of Sorpol 5029 (a registered trade mark of Toho Kagaku Co.) were thoroughly mixed. The mixtures were each added dropwise to 55 parts by weight of 200 mesh talc in a mortar while thoroughly stirring. Fourty-four wettable powders were thus obtained. They are each applied in a diluted form with water.

PREPARATION 3

Mixed emulsifiable concentrates

27 Parts by weight of each of the present compounds, (1) and (18), 3 parts by weight of N-(chrysanthemoxymethyl)-3,4,5,6-tetrahydrophthalimide (Neopinamin, a registered trade mark of Sumitomo Chemical Co.), 50 parts by weight of xylene and 20 parts by weight of Sorpol 2020 (a registered trade mark of Toho Kagaku Co.) were mixed in a proper order. Two uniform emulsifiable concentrates were thus obtained. They are each applied in a diluted form with water.

PREPARATION 4

Mixed wettable powders

20 Parts by weight of each of the present compounds, (1), (2), (18) and (19), 10 parts by weight of O,O-dimethyl-O-(3-methyl-4-nitrophenyl)-phosphorothioate (Sumithion, a registered trade mark of Sumitomo Chemical Co.) and 5 parts by weight of Sorpol SM-200 (a registered trade mark of Toho Kagaku Co.) were thoroughly mixed. The mixtures were each added to 70 parts by weight of 300 mesh talc in a mortar while thoroughly stirring. Four mixed wettable powders were thus obtained.

PREPARATION 5

Dusts

3 Parts by weight of each of the present compounds (1), (4), (7), (18), (21), (24), (34), (36), (37), (39), (42), (43), (46), (49), were dissolved in 20 parts by weight of acetone and then 97 parts by weight of 300 mesh diatomaceous earth were added thereto. After thorough mixing in a mortar while stirring, acetone was removed by evaporation. Fourteen dusts were thus obtained.

PREPARATION 6

Granular preparations

5 Parts by weight of each of the present compounds (1)–(4), (7), (18)–(21) and (24), 5 parts by weight of Toyolignin CT (a registered trade mark of Toyo Spinning Co.) and 90 parts by weight of GSM Clay (a registered trade mark of Zieklite Mining Co.) were thoroughly mixed in a mortar.

Then the mixtures were each mixed with water of 10 percent by weight based on the mixture, granulated by means of a granulator and air-dried. Ten granular preparations were thus obtained.

PREPARATION 7

Fine granules

2 Parts by weight of each of the present compounds, (1), (3), (6), (18), (20) and (23), 2 parts by weight of O,O-dimethyl-O-4-cyanophenylphosphorothioate (Cyanox, a registered trade mark of Sumitomo Chemical Co.), 5 parts by weight of Toyolignin CT (a registered trade mark of Toyo Spinning Co.) and 91 parts by weight of GSM Clay (a registered trade mark of Zieklite Mining Co.) were thoroughly mixed in a mortar. Then the mixtures were each mixed with water of 10 percent by weight based on the mixture, granulated by means of a granulator, and air-dried. Six fine granules were thus obtained.

PREPARATION 8

Water-based aerosols 0.3 Part by weight of each of the present compounds, (1) and (18), 0.2 part by weight of Chrysron (a registered trade mark of Sumitomo Chemical Co.), 13.5 parts by weight of deodorized kerosene and 1 part by weight of Atmos 300 (a registered trade mark for an emulsifier sold by Atlas Chemical Co.) were thoroughly mixed, and emulsified by an addition of 50 parts by weight of pure water. An aerosol container was then filled with the resulting emulsion and 35 parts by weight of a 3:1 mixture of deodorized butane to deodorized propane. Two water-based aerosols were thus obtained.

The present invention will be illustrated with reference to the following examples which are only given for the purpose of illustration and not to be interpreted as limiting.

EXAMPLE 1

(Compound No. 1)

15.1 Grams of 3-(O-ethyl-S-(n)-propylphosphoryloxy)-benzaldoxime was dissolved in 100 ml of isopropylether, and 3.4 g of methylisocyanate and a catalytic amount of triethylamine were added to the resulting solution in this order at room temperature and allowed to stand for 24 hours with occasional shaking.

Isopropylether was removed under a reduced pressure to obtain reddish brown, oily 3-(O-ethyl-S-(n)-propylphosphoryloxy)-benzaldoxime-N-methylcarbamate (Refractive Index $n_D^{22.5}$ 1.5422), as a residue, quantitatively.

| Elementary analysis: Calculated (%) | (as $C_{14}H_{21}N_2O_5PS$) | Found (%) |
|---|---|---|
| O  46.65 | | 46.45 |
| H  5.89 | | 6.01 |
| N  7.77 | | 7.98 |
| P  8.59 | | 8.85 |

EXAMPLE 2

(Compound No. 2)

Yellow, oily 4-(O-ethyl-S-(n)-propylphosphoryloxy)- benzaldoxime-N-methylcarbamate ($n_D^{24.0}$ 1.5426) was obtained in the same manner as described in Example 1.

| Elementary analysis: Calculated (%) | (as $C_{14}H_{21}N_2O_5PS$) | Found (%) |
|---|---|---|
| C  46.65 | | 46.36 |
| H  5.89 | | 6.03 |
| N  7.77 | | 7.85 |
| P  8.59 | | 8.99 |

EXAMPLE 3

(Compound No. 3)

Orange, oily 2-(O-ethyl-S-(n)-propylphosphoryloxy)-benzaldoxime-N-methylcarbamate ($n_D^{24.0}$ 1.5370) was obtained in the same manner as described in Example 1.

| Elementary analysis: Calculated (%) | (as $C_{14}H_{21}N_2O_5PS$) | Found (%) |
|---|---|---|
| C  46.65 | | 46.73 |
| H  5.89 | | 5.91 |
| N  7.77 | | 7.61 |
| P  8.59 | | 8.06 |

EXAMPLE 4

(Compound No. 9)

Orange, oily 4-(O-ethyl-S-(n)-propylphosphoryloxy)-2-methoxybenzaldoxime-N-methyl-carbamate ($n_D^{25.5}$ 1.5528) was obtained in the same manner as described in Example 1.

| Elementary analysis: Calculated (%) | (as $C_{15}H_{23}N_2O_6PS$) | Found (%) |
|---|---|---|
| C  46.14 | | 46.27 |
| H  5.95 | | 5.76 |
| N  7.18 | | 7.03 |
| P  7.93 | | 7.88 |

EXAMPLE 5

(Compound No. 4)

Yellow, oily 4-(O-ethyl-S-(n)-propylphosphoryloxy)-benzaldoxime-N-phenylcarbamate ($n_D^{24.5}$ 1.5884) was obtained in the same manner as described in Example 1.

| Elementary analysis: Calculated (%) | (as $C_{19}H_{23}N_2O_5PS$) | Found (%) |
|---|---|---|
| C  54.01 | | 54.16 |
| H  5.50 | | 5.29 |
| N  6.63 | | 6.53 |
| P  7.33 | | 7.10 |

EXAMPLE 6

(Compound No. 18)

15.2 Grams of 4-(O-ethyl-S-(n)-propylphosphoryloxy)-acetophenonoxime was dissolved in 100 ml of isopropylether, and 3.1 g of methylisocyanate and a catalytic amount of triethylamine were added to the resulting solution in this order at room temperature and allowed to stand for 24 hours with occasional shaking.

Isopropylether was removed under a reduced pressure to obtain pale yellow, oily 4-(O-ethyl-S-(n)-propylphosphoryloxy)-acetophenonoxime-N-methylcarbamate ($n_D^{20}$ 1.5480), as a residue, quantitatively.

| Elementary analysis: Calculated (%) | (as $C_{15}H_{23}N_2O_5PS$) | Found (%) |
|---|---|---|
| C  48.12 | | 47.69 |
| H  6.19 | | 5.81 |
| N  7.48 | | 7.19 |
| P  8.27 | | 8.14 |

EXAMPLE 7

(Compound No. 19)

Pale yellow, oily 3-(O-ethyl-S-(n)-propylphosphoryloxy)-acetophenonoxime-N-methylcarbamate ($n_D^{20}$ 1.5462) was obtained in the same manner as described in Example 1.

| Elementary analysis: Calculated (%) | (as $C_{15}H_{23}N_2O_5PS$) | Found (%) |
|---|---|---|
| C  48.12 | | 48.12 |
| H  6.19 | | 5.93 |
| N  7.48 | | 7.66 |
| P  8.27 | | 8.19 |

EXAMPLE 8

(Compound No. 20)

Pale yellow, oily 4-(O-ethyl-S-(N)-propyl-phosphoryloxy)-acetophenonoxime-N-ethylcarbamate ($n_D^{23}$ 1.5402) was obtained in the same manner as described in Example 1.

| Elementary analysis: Calculated (%) | (as $C_{16}H_{25}N_2O_5PS$) | Found (%) |
|---|---|---|
| C  49.47 | | 49.18 |
| H  6.49 | | 6.60 |
| N  7.21 | | 7.45 |
| P  7.97 | | 8.06 |

EXAMPLE 9

(Compound No. 21)

Pale yellow, oily 3-(O-ethyl-S-(n)-propylphosphoryloxy)-acetophenonoxime-N-ethylcarbamate ($n_D^{23}$ 1.5394) was obtained in the same manner as described in Example 1.

| Elementary analysis: Calculated (%) | (as $C_{16}H_{25}N_2O_5PS$) | Found (%) |
|---|---|---|
| C  49.47 | | 49.28 |
| H  6.49 | | 6.40 |
| N  7.21 | | 7.25 |
| P  7.97 | | 7.99 |

EXAMPLE 10

(Compound No. 6)

Yellow, oily 3-(O-ethyl-S-(n)-propylphosphoryloxy)-benzaldoxime-N-ethylcarbamate ($n_D^{21.0}$ 1.5410) was obtained in the same manner as described in Example 1.

| Elementary analysis: Calculated (%) | (as $C_{13}H_{23}N_2O_5PS$) | Found (%) |
|---|---|---|
| C | 48.11 | 47.72 |
| H | 6.20 | 5.90 |
| N | 7.48 | 7.28 |
| P | 8.27 | 8.23 |

EXAMPLE 11

(Compound No. 7)

Yellow, oily 4-(O-ethyl-S-(n)-propylphosphoryloxy)-benzaldoxime-N-ethylcarbamate ($n_D^{27.5}$ 1.5403) was obtained in the same manner as described in Example 1.

| Elementary analysis: Calculated (%) | (as $C_{13}H_{23}N_2O_5PS$) | Found (%) |
|---|---|---|
| C | 48.11 | 47.91 |
| H | 6.20 | 6.11 |
| N | 7.48 | 7.20 |
| P | 8.27 | 8.00 |

EXAMPLE 12

(Compound No. 12)

Yellow, oily 4-(O-ethyl-S-(n)-butylphosphoryloxy)-benzaldoxime-N-methylcarbamate ($n_D^{20.0}$ 1.5444) was obtained in the same manner as described in Example 1.

| Elementary analysis: Calculated (%) | (as $C_{13}H_{23}N_2O_5PS$) | Found (%) |
|---|---|---|
| C | 48.11 | 48.17 |
| H | 6.20 | 6.20 |
| N | 7.48 | 7.46 |
| P | 8.27 | 8.18 |

EXAMPLE 13

(Compound No. 14)

Orange, oily 2-(O-ethyl-S-(n)-propylphosphoryloxy)-benzaldoxime-N-ethylcarbamate ($n_D^{20.0}$ 1.5420) was obtained in the same manner as described in Example 1.

| Elementary analysis: Calculated (%) | (as $C_{13}H_{23}N_2O_5PS$) | Found (%) |
|---|---|---|
| C | 48.11 | 48.38 |
| H | 6.20 | 6.05 |
| N | 7.48 | 7.51 |
| P | 8.27 | 8.00 |

EXAMPLE 14

(Compound No. 34)

Reddish brown, oily 4-(O-ethyl-S-(n)-propylphosphoryloxy)-benzaldoxime-N-isopropylcarbamate ($n_D^{20.0}$ 1.5370) was obtained in the same manner as described in Example 1.

| Elementary analysis: Calculated (%) | (as $C_{14}H_{23}N_2O_5PS$) | Found (%) |
|---|---|---|
| C | 49.47 | 49.48 |
| H | 6.50 | 6.54 |
| N | 7.21 | 7.34 |
| P | 7.97 | 8.21 |

EXAMPLE 15

(Compound No. 35)

Yellow, oily 2-(O-ethyl-S-(n)-propylphosphoryloxy)-benzaldoxime-N-iso-propylcarbamate ($n_D^{20.0}$ 1.5350) was obtained in the same manner as described in Example 1.

| Elementary analysis: Calculated (%) | (as $C_{14}H_{23}N_2O_5PS$) | Found (%) |
|---|---|---|
| C | 49.47 | 49.35 |
| H | 6.50 | 6.47 |
| N | 7.21 | 7.25 |
| P | 7.97 | 7.45 |

EXAMPLE 16

(Compound No. 36)

Pale yellow, oily 2-methoxy-4-(O-ethyl-S-(n)-propylphosphoryloxy)-benzaldoxime-N-phenylcarbamate ($n_D^{25.5}$ 1.5848) was obtained in the same manner as described in Example 1.

| Elementary analysis: Calculated (%) | (as $C_{20}H_{25}N_2O_5PS$) | Found (%) |
|---|---|---|
| C | 53.08 | 52.66 |
| H | 5.58 | 5.35 |
| N | 6.19 | 6.06 |
| P | 6.84 | 6.62 |

EXAMPLE 17

(Compound No. 37)

Orange, oily 2-(O-ethyl-S-(n)-butylphosphoryloxy)-benzaldoxime-N-methylcarbamate ($n_D^{20.0}$ 1.5459) was obtained in the same manner as described in Example 1.

| Elementary analysis: Calculated (%) | (as $C_{13}H_{23}N_2O_5PS$) | Found (%) |
|---|---|---|
| C | 48.11 | 48.18 |
| H | 6.20 | 6.20 |
| N | 7.48 | 7.48 |
| P | 8.27 | 8.18 |

The oximes, a starting material, used according to the present invention can easily be prepared by reacting the corresponding ketones or aldehydes with hydroxylamine.

Preparation of intermediate (1) 3-(O-Ethyl-S-(n)-propylphosphoryloxy)-benzaldoxime To 16.8 g of a 10 % aqueous caustic soda solution were added 2.9 g of hydroxylamine hydrochloride at below 10°C, and then 10.1 g of 3-(O-ethyl-S-(n)-propylphosphoryloxy)-benzaldehyde at 15° to 20°C. The resulting solution was stirred for 1 hour at 25°C. Separated oily matter was dissolved in benzene, washed with water and freed of benzene under a reduced pressure to obtain 10.0 g of reddish brown, oily aimed matter ($n_D^{20.0}$ 1.5566) as a residue.

| Elementary analysis: Calculated (%) | (as $C_{12}H_{18}NO_4PS$) | Found (%) |
|---|---|---|
| C | 47.52 | 47.51 |
| H | 5.98 | 5.83 |
| N | 4.62 | 4.57 |
| P | 10.21 | 10.05 |

(2) 4-(O-Ethyl-S-(n)-propylphosphoryloxy)-acetophenonoxime

Yellow, oily aimed matter ($n_D^{23.0}$ 1.4211) was obtained in the same manner as described in (1).

| Elementary analysis: Calculated (%) | (as $C_{13}H_{20}NO_4PS$) | Found (%) |
|---|---|---|
| C | 49.20 | 48.87 |
| H | 6.35 | 6.41 |
| N | 4.41 | 4.82 |
| P | 9.76 | 9.98 |

(3) 3-(O-Ethyl-S-(n)-propylphosphoryloxy)-acetophenonoxime

Yellow, oily aimed matter ($n_D^{23.0}$ 1.4372) was obtained in the same manner as described in (1).

| Elementary analysis: Calculated (%) | (as $C_{13}H_{20}NO_4PS$) | Found (%) |
|---|---|---|
| C | 49.20 | 49.30 |
| H | 6.35 | 6.17 |
| N | 4.41 | 4.71 |
| P | 9.76 | 9.59 |

TEST EXAMPLE 1

Lethal effect on tobacco cut worm (*Spodoptera litura*)

Each of 50 % emulsifiable concentrates of the present compounds, (1) and (18) was applied on chinese cabbage seedlings which had elapsed one month after sowing. Then the seedlings were cut, air-dried and placed in a glass Petri dish. Third instar larvae of tobacco cut worm were released in the dish and the death and alive after 48 hours were observed, from which $LC_{50}$ values were calculated. The results are as shown in Table 1.

Table 1

| Compound No. | | $LC_{50}$ (ppm) |
|---|---|---|
| (1) | | 30 |
| (18) | | 60 |
| Standard | EPN[1] | 100 |
| compound | DDVP[2] | 260 |

Note:
[1]Commercially available insecticide (O-ethyl-O-p-nitrophenylphosphonothioate)
[2]Commercially available insecticide (2,2-dichlorovinyldimethyl phosphate)

TEST EXAMPLE 2

Lethal effect on diamond-back moth (*Plutella maculipennis*)

A 250 fold dilute solution of each 50 % emulsifiable concentrate of the present compounds shown in Preparation 1 was applied on chinese cabbage seedlings which had elapsed 1 month after sowing. Then the seedlings were cut, air-dried and placed in a glass Petri dish. Fourth instar larvae of diamond-back moth were released in the dish and the death and alive after 48 hours were observed, from which the mortality was calculated. The results are as shown in Table 2.

Table 2

| Compound No. | Mortality (%) | Compound No. | Mortality (%) |
|---|---|---|---|
| (1) | 100 | (20) | 100 |
| (2) | 100 | (21) | 100 |
| (3) | 100 | (22) | 100 |
| (4) | 100 | (24) | 100 |
| (5) | 100 | (25) | 100 |
| (6) | 100 | (28) | 100 |
| (9) | 100 | (30) | 100 |
| (10) | 100 | (33) | 100 |
| (13) | 100 | (34) | 100 |
| (17) | 100 | (35) | 100 |
| (18) | 100 | (36) | 100 |
| (19) | 100 | (37) | 100 |
| (40) | 100 | (47) | 100 |
| (45) | 100 | (48) | 100 |

TEST EXAMPLE 3

Acaricidal activity on carmine mites (*Tetranychus telarius*)

Carmine mite females were made parasitic on leaves of the potted kidney bean (2-leaf stage) which had elapsed 9 days after sowing, in a proportion of 10–15-/leaf, and bred at 27°C for a week in a constant temperature room. Then numerous carmine mites were found to be bred at various growth stages. At this time, a 200 fold dilute solution of each wettable powder of the present compounds shown in Preparation 2 was sprayed in a proportion of 10 cc/pot by means of a turn table. After 10 days the degree of damage of kidney bean and the degree of breeding of carmine mite were observed and classified into five grades (−, +, ++, +++, ++++). The results are as shown in Table 3.

The degree of damage of kidney bean leaves:
−; damage is hardly observed,
++++; leaves are dead,
and the degree of damage between the two extremes was classified into three grades.

The degree of breeding of carmine mites:
−; the alive are less than 10,
++++; the alive are numerous,
and the degree of breeding between the two extremes was classified into three grades.

Table 3

| Compound No. | Degree of damage | Degree of breeding |
|---|---|---|
| (1) | − | − |
| (2) | − | − |
| (3) | − to + | + |
| (6) | − | − to + |
| (15) | − | − |

Table 3—Continued

| Compound No. | Degree of damage | Degree of breeding |
|---|---|---|
| (18) | − | − |
| (19) | − to + | + |
| (20) | − | − |
| (31) | − | − to + |
| (33) | − | − |
| (34) | − | − |
| (35) | − | − |
| (36) | − | − |
| (37) | − | − to + |
| (44) | − | − |
| (47) | − | − |
| (48) | − | − to + |

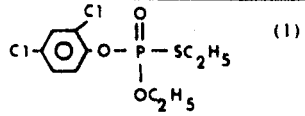

| | | |
|---|---|---|
| (1) | + to ++ | + to ++ |

Control
| | | |
|---|---|---|
| Galecron (2) | − to + | + to ++ |
| No treatment | ++++ | ++++ |

Note:
(1) Well-known compound
(2) N'-(2-methyl-4-chlorophenyl)-N,N-dimethyl-formamidine

TEST EXAMPLE 4

Acaricidal activity on carmine mite (*Tetranychus telarius*)

Each of 50 % emulsifiable concentrates of the present compounds (1), (2) and (4), was diluted to a predetermined concentration. Leaves of kidney bean on which carmine mite adults had previously been made parasitic were dipped in the diluted solution for 1 minute. Water was given to the leaves not to kill them, and the death and alive after 48 hours were observed to calculate the mortality, from which values of $LC_{50}$ were obtained. The results are as shown in Table 4.

Table 4

| Compound No. | $LC_{50}$ (ppm) |
|---|---|
| (1) | 25 |
| (2) | 21 |
| (4) | 74 |
| (18) | 29 |
| (19) | 37 |
| (21) | 51 |

TEST EXAMPLE 5

Effect on nematode (*Panagrellus redivivus*)

Nematodes separated from food according to Baermann's method was dipped in a solution containing 500 ppm of each of the present compounds (a 1000 fold dilute solution of 50 % emulsifiable concentrate). The death and alive after 24 hours were observed, from which the mortality was calculated. The results are as shown in Table 5.

Table 5

| Compound No. | Mortality (%) | Compound No. | Mortality (%) |
|---|---|---|---|
| (1) | 100 | (18) | 100 |
| (2) | 100 | (19) | 100 |
| (3) | 100 | (20) | 100 |
| (4) | 100 | (21) | 100 |
| (9) | 100 | (23) | 100 |
| (10) | 100 | (26) | 100 |
| (12) | 100 | (27) | 100 |
| (14) | 100 | (32) | 100 |
| (16) | 100 | | |

TEST EXAMPLE 6

Insecticidal activity in the green house

Armyworms, cutworms, cabbages worm and diamond-back moths were artificially made parasitic on chinese cabbage which had been grown up in a green house. Then the house (2 m in height) was divided into spaces (30 m² in area, 2 m in height), and 10 g of wettable powder obtained in Preparation 2 were smoken in a SEARCH in each divided space. The spread of damage by the insects was hardly observed with any wettable powder.

TEST EXAMPLE 7

Insecticidal activity on chrysanthemum aphids (*Macrosiphoniella sanborni Gillette*)

Water-based aerosols obtained in Preparation 8 were, each sprayed for 1 second on the potted chrysanthemum on which a large number of chrysanthemum aphids had been made parasitic. After 24 hours, the alive was hardly observed.

TEST EXAMPLE 8

Insecticidal activity on Northern house mosquito (*Culex pipiens pallens*)

The emulsifiable concentrates of the present compounds, (1), (2), (3), (4), (18), (19), (20) and (21), obtained in Preparation 1, were each diluted 500,000 times with water. 2 Liters of each test emulsion so prepared were taken in a polystyrene case of 23 cm × 30 cm in area and 6 cm in depth, and about 100 full grown larvae of Northern house mosquito (*Culex pipiens pallens*) were liberated therein. By the next day, more than 90 % of the larvae were killed with any concentrate.

What we claim is:

1. Thio (dithio)-phosphorate of the formula,

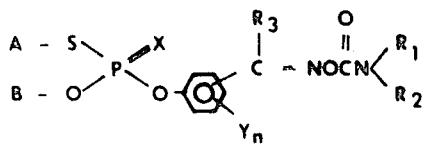

wherein A represents an alkyl having up to 6 carbon atoms; B represents lower alkyl having up to 4 carbon atoms; Y represents halogen, methoxy or ethoxy; X represents oxygen; $R_1$ represents alkyl having up to 6 carbon atoms, phenyl, phenyl substituted by halogen or phenyl substituted by lower alkyl having up to 4 carbon atoms; $R_2$ represents hydrogen or alkyl having up to 6 carbon atoms; $R_3$ represents hydrogen or alkyl having up to 6 carbon atoms; and n represents 0, 1 or 2.

2. Thio (dithio)-phosphorate of the formula,

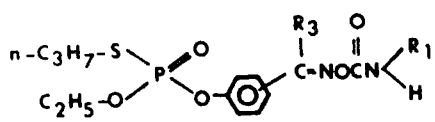

wherein $R_1$ represents methyl or ethyl; $R_3$ represents hydrogen or methyl.

3. The compound of the formula,

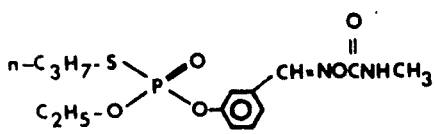

4. The compound of the formula,

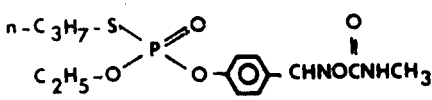

5. The compound of the formula,

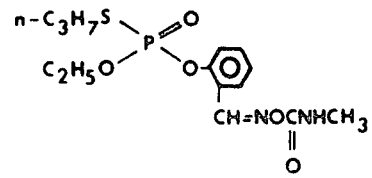

6. The compound of the formula,

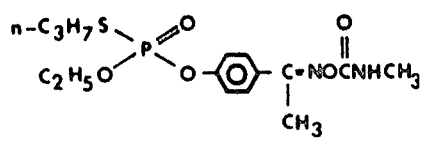

7. The compound of the formula,

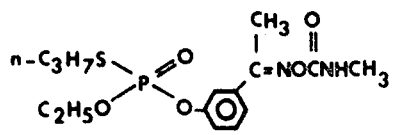

8. The compound of the formula,

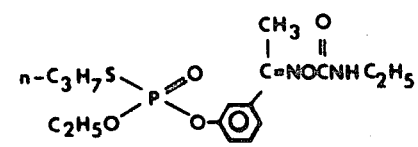

* * * * *